US012721796B2

(12) United States Patent
Meehan et al.

(10) Patent No.: US 12,721,796 B2
(45) Date of Patent: Sep. 1, 2026

(54) NON-SILICONE SILKY FRAGRANCE PRODUCT FOR HAIR

(71) Applicant: AKI, Inc., Chattanooga, TN (US)

(72) Inventors: Matthew Meehan, Teaneck, NJ (US); David O' Halloran, Somerset, NJ (US)

(73) Assignee: AKI, Inc.

( * ) Notice: Subject to any disclaimer, the term of this patent is extended or adjusted under 35 U.S.C. 154(b) by 947 days.

(21) Appl. No.: 17/884,982

(22) Filed: Aug. 10, 2022

(65) Prior Publication Data

US 2023/0072314 A1 Mar. 9, 2023

Related U.S. Application Data

(60) Provisional application No. 63/260,190, filed on Aug. 12, 2021.

(51) Int. Cl.

| | |
|---|---|
| ***A61K 8/34*** | (2006.01) |
| ***A61K 8/04*** | (2006.01) |
| ***A61K 8/67*** | (2006.01) |
| ***A61K 8/9794*** | (2017.01) |
| ***A61Q 13/00*** | (2006.01) |

(52) U.S. Cl.

CPC .............. *A61K 8/345* (2013.01); *A61K 8/046* (2013.01); *A61K 8/673* (2013.01); *A61K 8/678* (2013.01); *A61K 8/9794* (2017.08); *A61Q 13/00* (2013.01); *A61K 2800/34* (2013.01); *A61K 2800/49* (2013.01)

(58) Field of Classification Search

CPC .......... A61Q 5/00; A61Q 13/00; A61K 8/678; A61K 8/922; A61K 8/345; A61K 8/046; A61K 8/9794; A61K 8/673; A61K 2800/49; A61K 2800/34

USPC ........................................................... 512/2

See application file for complete search history.

(56) References Cited

U.S. PATENT DOCUMENTS

2012/0164092 A1* 6/2012 Kurashima .............. A61K 8/86 424/70.11

FOREIGN PATENT DOCUMENTS

| | | | | |
|---|---|---|---|---|
| JP | 2005-206552 A | | 8/2005 | |
| JP | 2007-529445 A | | 10/2007 | |
| JP | 2012-254946 A | | 12/2012 | |
| JP | 2014-172908 A | | 9/2014 | |
| JP | 2016-179975 A | | 10/2016 | |
| WO | 1996/012467 A1 | | 5/1996 | |
| WO | WO-9612467 A1 | * | 5/1996 | ............ A61Q 13/00 |
| WO | 2005/046696 A1 | | 5/2005 | |
| WO | 2014/016349 A1 | | 1/2014 | |
| WO | WO-2016075328 A1 | * | 5/2016 | ............ A61K 8/345 |
| WO | 2023/018798 A1 | | 2/2023 | |

OTHER PUBLICATIONS

International Search Report and Written Opinion issued in International Patent Application No. PCT/US22/39955 mailed on Oct. 24, 2022.

Anonymous, "Bounce Back Reactivating Mist", GNPD, MINTEL, (Oct. 20, 2020), Database accession No. 8200959, URL: https://www.gnpd.com/sinatra/recordpage/8200959/.

First Examination Report dated Feb. 22, 2024 in Canadian application No. 3,225,408.

Subsequent Examination Report dated Feb. 14, 2025 in Canadian application No. 3,225,408.

Examination Report dated Mar. 6, 2024 in Australian application No. 2022328389.

Extended European Search Report dated Nov. 27, 2024 in European application No. 22856561.0.

Office action dated Feb. 20, 2025 in Chilean application No. 2024-00058.

Office action dated Aug. 21, 2024 in Japanese application No. 2024-501234.

Office Action dated Feb. 19, 2025 in Japanese application No. 2024-501234.

Communication pursuant Article 94(3) EPC dated Jun. 25, 2025 in European application No. 22856561.0.

* cited by examiner

*Primary Examiner* — Jessica Whiteley

(74) *Attorney, Agent, or Firm* — Rivkin Radler LLP

(57) ABSTRACT

A non-aerosol and non-oily fragrance product comprising a uniformly diffusive hair mist spray formulation including: about 0.1-15.0 percent by weight fragrance, about 5.0-10.0 percent by weight solubilizer, about 3.0-4.9 percent by weight ethylhexylglycerin, about 0.5-5.0 percent by weight propanediol, about 38.0-50 percent by weight alcohol, and up to about 45.0 percent by weight water (aqua). The product can also include about 0.01-15.0 percent by weight additives such as amino acid complex. The hair mist product is free of silicone, which can weigh down the hair, and contains no quaternium or cationic compounds. The hair mist spray is VOC compliant, exhibits long-lasting fragrance notes, and enhances hair shine with a non-greasy and silky luxurious feel.

20 Claims, No Drawings

NON-SILICONE SILKY FRAGRANCE PRODUCT FOR HAIR

CROSS REFERENCE TO RELATED APPLICATION(S)

The present U.S. non-provisional application claims priority to U.S. Provisional Application Ser. No. 63/260,190, filed Aug. 12, 2021, which is incorporated herein by reference in its entirety for all purposes.

FIELD OF THE APPLICATION

The disclosed subject matter relates to a non-silicone and non-oily fragrance product for use as a hair mist or spray that imparts shine and silky feel to hair with extended release of fragrance notes. Aspects of the present disclosure also relate to methods for making and using such non-silicone silky fragrance hair mist product.

BACKGROUND

Fragrant mists or sprays are commonly used to deliver fragrance to a user's hair. These compositions, however, often contain silicone or other ingredients that can create an oily residue or heavy feel, oftentimes weighing down on the hair, even after cleansing one's hair.

Silicone is known to build up in the hair, resulting in dry feel and heavy appearance. Hair may also become weakened and more prone to breakage from silicone-based hair products. In addition, silicone-based hair products are more difficult to remove from hair even with a regular wash. Most silicones are non-soluble, which means they cannot be readily removed nor penetrated with water. Silicones also prevent moisture from penetrating the hair resulting in dry feel and dull appearance. Many silicone hair products are also not water-soluble and hence, are not easily removed from the hair. Silicones can build up on the scalp and can even clog or suffocate your hair follicles, causing inflammation and persistent flakes. Therefore, it stands to reason that a silicone-free formula for hair products can help improve overall scalp health. It is known that healthy hair begins with a healthy scalp.

Therefore, inclusion of alcohol in hair products provides longer lasting integrity, which also remain bacteria-free, among other contemplated and known benefits. Usage of alcohol(s) to deliver fragrance in combination with other ingredients in a hair product permits the delivery of a clear formulation-based product with uniform application on the hair. A hydroalcoholic solution is therefore desirable in a mist spray formulation, specifically a non-aerosol hair product formulation, which enhances the safety levels of such use, especially since sprayed around a user's face when applied to hair. The effects of spray cosmetics can include symptoms such as dizziness, breathlessness, headaches and tiredness. People with lung diseases such as chronic obstructive pulmonary disease or asthma are particularly susceptible and may have symptoms worsen. While long-term effects are less well-known, studies have indicated ill health effects to long-term aerosol spray users.

Inhaled aerosols and particulate ingredients are known to present different health risks depending on their size and strength. The smaller they are, the deeper they can penetrate into our lungs. Other factors such as particle type, airborne concentration and exposure frequency and duration are also important factors. People working with these sorts of products, typically in hair and beauty salons, have the greatest potential for repeated exposure. However, consumers may also be at risk of exposure due to occasional inhalation either at beauty salons or at home.

Therefore, there is a need for non-aerosol hair spray formulations that can reduce the known health risk factors associated with fine aerosol hair sprays.

Some of the purported benefits of a hydroalcoholic-based hair formulations include that such formulations solubilize the fragrance into a clear high-water solution and avoid the use of preservatives known to be of concern. The incorporation of alcohol prevents the formulation to render the hair (upon application of the hair mist spray), to be non-sticky and permit a fine-mist application with inclusion in certain embodiments, of fine fragrance notes which are extended release. Such extended release is generally characterized a hydroalcoholic formula with additives that extend the release of volatile top notes, which in effect, slows diffusion thereof. In addition, the hair is not weighed down and dries quickly and smoothly upon application with the disclosed hair mist spray.

The Personal Care Products Counsel (PCPC) (and, for example the California Air Resources Board (CARB) working with PCPC along with over 600 member companies with strong interest in the applicable of new VOC regulations) are seeking to reduce VOC emission levels for personal care product categories, with a goal to reach a 50% VOC limit in hair finishing products by Jan. 1, 2023. Longer-term PCPC goals include proposed VOC limits for 2031 with 50% VOC maximum and threshold levels, including products with fragrance levels of 0-10%, including those in the 7-10% fragrance levels, and therefore, seek to mandate manufacturers of such products, to comply with a maximum VOC level of 50% instead of 55%.

Thus, there is a need for a non-silicone and non-oily fragrance product that can be sprayed or misted onto a user's hair that is long-lasting, has a silky feel, manifest longer-lasting fragrance notes and more readily and easily washes and rinses from the hair. Further, there is a need for a non-aerosol type spray that has longer lasting effects, fosters uniform application on the hair, imparts shine and improved fragrance lift. Aerosol type hair sprays are known to deplete the ozone layer or for emitting harmful chemical compounds into the environment and thus, there is a need to reduce such emissions by reduction of such emissions by use of formulations associated with non-aerosol hair sprays or mists.

There is a further need for new and improved formulations for use on hair, in the form of non-aerosol sprays, that offer consumers unique and long-lasting sensory experience, better tactile experience, product performance, texture, consistency and better fragrance uniform diffusion, that is more pleasing to consumers, environmentally safe and healthy for hair with reduced VOC limits. Such improved formulations will reduce the resins implemented in such hair finishing products. The use of mechanical pump sprays is safer for fragrance mists emitted around a use, especially one's face. Studies show that the use of finer aerosol mists and specifically, the propellants allow for the inhalation of the propellants (for example, butane and isobutane). These aerosols reduce the particular size of the ingredients in the fragrance and may affect the respiratory area.

SUMMARY

The disclosed subject matter provides, according to some embodiments, a non-silicone, non-oily fragrance hair mist or spray product. The hair mist product contains about 0.1-15.0 percent by weight fragrance, about 5.0-10.0 percent by weight solubilizer, about 3.0-4.9 percent by weight ethylhexylglycerin, about 0.5-5.0 percent by weight propanediol, about 38-50 percent by weight alcohol, and about 38-45 percent by weight water. Some embodiments also contain about 0.01-15.0 percent by weight additives, such as amino acid complex.

Ethylhexylglycerin in certain aspects or embodiments, is a synthetic skin-softening agent. Ethylhexylglycerin can also be used as a preservative and carrier/suspending agent that boosts the efficacy of other preservatives, such as phenoxyethanol. Ethylhexylglycerin has been shown to have mild humectant properties leading to improved skin hydration without a sticky feel. Over time, silicone can also build up on your hair, resulting in a dry feel and dull appearance. One may even notice that your hair becomes weaker and more prone to breakage. If one is using a form of silicone that isn't water-soluble, it can be really difficult to remove it with a regular wash. Hence, such hair mist formulation avoids the ill-effects of silicone and enhances the efficacy of other preservatives, such as phenoxyethanol.

Such formulation comprises perfume compounds including the combination of propanediol and ethylhexylglycerin, that enhances the fragrance prominence, distinctiveness, and substantivity, without rendering the hair feel as heavy or oily, and is characterized by more pronounced intensity, longevity, and character of original fragrance notes, coupled with a silky luxurious feel when applied to hair in a non-aerosol mist or spray release formulation. Mechanical pump products are easier to fill and ship, than aerosol products. When the mechanical pump selection and related mechanism thereof is used, it will improve application since it is more targeted, as opposed to aerosol-type mists which are messier, due to the pressure inside the container, which often does not allow for targeted delivery of the hair mist.

The foregoing summary and the following detailed description are exemplary and are intended to provide an explanation of the disclosed subject matter. The purpose and advantages of the disclosed subject matter are set forth in the following description, and additional advantages may be obtained by the practice and knowledge of those skilled in the art based on this description.

DETAILED DESCRIPTION

The hair mist product presented herein may be employed by a user to obtain the benefits of the fragrance without the disadvantages associated with using a silicone-based spray formulation. The hair mist non-aerosol product is particularly suited for users who desire longer-lasting fragrance included associated fragrance notes, without an oily or heavy feel on the hair.

Silicones are known to build up on hair and not rinse off easily. In addition, silicones do not emulsify and easily create clear systems that have the recited benefits of the disclosed hair mist product.

In addition, regulatory requirements for hair products only allow a maximum level of VOC (volatile organic compounds) this regulation has restricted and will restrict further in the near future, the use of many aerosol hairsprays and changed formulations to be mechanical sprays rather than propellant-based application. Because water based or high-water systems can be very messy to spray the use of ethanol is hard to overcome. In certain aspects or embodiments, the disclosed hair mist formulation embraces the use of low levels ethanol because it combines a non-silicone blend of silky and hair enhancing additives, while also adhering to VOC regulations Since the primary purposes of these formulations are to fragrance the hair with a high level of fragrance and enhance shine simultaneously, the alcohol allows for an elegant fine mist application and for the formulation to dry quickly and smoothly. Further, in certain aspects or embodiments the fine mist spray formulation, is combinable in one formulation with finer and even luxury type fragrances and/or fragrance notes/ingredients for an optimal sensory experience for the user. Single note or less complex fragrances are an increasing trend, and because they are not as nuanced as more "complete or blended" fragrances, maintaining fragrance intensity is even more important, so the consumer can enjoy the fragrance longer and more completely. Top notes of a fragrance are the first to dissipate and therefore, making a fragrance last longer is a matter of managing the diffusion. The disclosed hair mist product formulation is effective at accomplishing this (i.e. making a fragrance last longer with managed diffusion), especially on a substrate, such as hair, which has a high degree of air exposure and movement.

In certain aspects or embodiments, the alcohol along with the other materials also solubilize the fragrance into a clear high-water solution and avoids the use of preservatives of concern. The incorporation of alcohol also prevents the formulation from being non-sticky and allowing a fine mist application to not weigh down the hair. Clarity is often associated with very high levels of solubilizers in high water systems, particularly when a high level of fragrance is incorporated. Therefore, maintaining clarity in these systems, while imparting positive attributes of shine, silky feeling, and long-lasting fragrance, is always a difficult challenge.

In accordance with an embodiment, the disclosed hair mist formulation comprises perfume compounds including the combination of propanediol and ethylhexylglycerin that enhances the fragrance prominence, distinctiveness, and substantivity, without rendering the hair feel as heavy or oily, and is characterized by more pronounced intensity, longevity, and character of original fragrance notes, coupled with a silky luxurious feel when applied to hair in a non-aerosol mist or spray release formulation with enhanced and sustained fragrance lift, including the lift of original fragrance notes.

More specifically, the disclosed subject matter relates to a non-silicone and non-oily fragrance hair mist or spray product containing about 0.1-15.0 percent by weight fragrance, about 5.0-10.0 percent by weight solubilizer, about 3.0-4.9 percent by weight ethylhexylglycerin, about 0.5-5.0 percent by weight propanediol, about 38.0-50.0 percent by weight alcohol, and up to about 45.0 percent by weight water (aqua). In certain embodiments, the upper range percent by weight of alcohol is 55 percent. Some embodiments also contain 0.01-15.0 percent by weight of additives, such as amino acid complex.

The fragrance ingredient of the hair mist product can be any suitable fragrance (for example, parfum) for hair mist sprays, including essential oils, in certain embodiments and other fragrance single note or accord combination ingredients, known to those of skill in the art. As used herein, "fragrance" is defined and/or used to indicate any odoriferous or scented material that is generally considered pleasant to fragrance consumers. Any fragrance that is cosmetically acceptable may be used in the composition. For example, the fragrance may be one that is a liquid at room temperature. In a preferred embodiment, the perfume compounds including fragrance notes, are present from about 1 to lower than 20% wt., and more preferably between 5 to 13% wt.

In certain aspects or embodiments, a wide variety of chemicals are known as fragrances, including aldehydes, ketones, and esters, and can be included in the disclosed formulation. More commonly, naturally occurring plant and animal oils and exudates comprising complex mixtures of various chemical components are known for use as fragrances. Non-limiting examples of the fragrances useful herein include pro-fragrances such as acetal pro-fragrances, ketal pro-fragrances, ester pro-fragrances, hydrolyzable inorganic-organic pro-fragrances, and mixtures thereof. The fragrances may be released from the pro-fragrances in a number of various ways. For example, the fragrance may be released as a result of simple hydrolysis, by a shift in an equilibrium reaction, by a pH-change, or by enzymatic release. Embodiments of the present disclosure helps prevent and/or slow down any such deterioration to original fragrance notes. The fragrances may be relatively simple in their chemical make-up, comprising a single chemical, or may comprise highly sophisticated complex mixtures of natural and synthetic chemical components, all chosen to provide any desired odor or scent.

In accordance with embodiments, the solubilizer ingredient of the hair mist product can be any suitable solubilizer for hair mist sprays. For example, a preferred solubilizer is a blend of PEG-40 hydrogenated castor oil, trideceth-9, and water (such as for example, Symrise #611674), but other suitable solubilizers known in the art can be used. The solubilizer used can be a combination of standard fragrance solubilizers used in the industry to solubilize fragrances or the combination of fragrance solubilizers and alcohol, that result in maintaining clarity of the fragrance in a high-water system. The selection of the solubilizer is intended to result in a smoother application and permit a clear formula in a low-alcohol high water formulation. The selection of solubilizer in certain aspects or embodiments, results in a smoother application and permits a clear formula in a low alcohol combined with high water formulation.

In certain aspects or embodiments, the ethylhexylglycerin ingredient of an example hair mist product, also known as octoxyglycerin, is a glyceryl ether with IUPAC name 3-[(2-Ethylhexyl)oxy]-1,2-propanediol. Commercial versions of ethylhexylglycerin such as sensiva SC 50 may be used in certain aspects or embodiments. Common use of ethylhexylglycerin in cosmetics is as a preservative or preservative enhancer. Ethylhexylglycerin is also used as a deodorant. Ethylhexylglycerin in combination with propanediol and triethyl citrate reduces the tack (or tackiness) of the water and solubilizer combination, while in certain aspects or embodiments, also imparts greater sparkly shine to the hair and/or long-lasting efficacy of the fragrance when applied on the hair surface. The hydroalcoholic formula with additives, extends the release of volatile top notes and slows diffusion thereof.

The proposed fragrance threshold by Personal Care Products Counsel (PCPC) and CARB, has been reduced from 10% to 7% as expected for 2023, for example, for all non-aerosol products. CARB has further proposed a reduction of VOC in hair shine products, from current 55% to 50% by 2029. Hair finishing sprays or hair sprays are expected to meet the 50% VOC limit by 2023. It is noted that this combination with propanediol, slows down the volatility of the fragrance and enhances the duration and hair shine. With expected reductions to VOC thresholds for various fragrance-based products, fine fragrance products, and personal fragrance products, including for example, hair shine products, the disclosed embodiment of the hair mist product is formulated to meet such proposed VOC requirements. PCPC is proposing 10% to 7% proposed fragrance reduction for all non-aerosol products. The 7% threshold will cover significantly more of the iconic finer fragrances. These reduced VOC emissions levels are important for personal care product categories and formulating the present hair mist spray takes into account product integrity, stability, safety and ultimately consumer acceptability standards as guidelines that parallel for example, those set by CARB and PCPC member companies that are presently aiming to reduce VOC emissions. The present hair mist formulation is contemplated with these proposed personal hair product VOC guidelines, that are being set and are considered important to the protection of human health and the environment.

Ethylhexylglycerin is generally multipurpose and enhances the fragrance duration but has use restrictions of less than 5 percent when spraying around the eye area. When used in combination with propanediol it boosts the substantivity and release of the fragrance (and/or fragrance notes) more significantly.

More specifically, in certain aspects or embodiments, and/or in exemplary preferred embodiments of the disclosed formulation of non-silicone silky fragrance hair mist product and/or carrier, ethyl hexyl glycerin (or ethylhexylglycerin), which is a glyceryl ether, imparts several benefits. Ethyl hexyl glycerin is a colorless, clear liquid preservative derived from vegetable glycerin, often coconut or a vegetable-derived oil. It has become an alternative for parabens and sulfates in hair and skin products, which are necessary for water-based skincare or cosmetic products in order to prevent bacterial or fungal overgrowth and ensure product safety. While it can be derived from animal sources, it mainly comes from plant-derived sources of glycerin, such as soybean or palm. In addition, ethyl hexyl glycerin in example embodiments of the disclosed fragrance carrier formulation, acts as a booster and fixative for fragrances.

The ingredient, ethyl hexyl glycerin, is represented by example formula (1) provided below:

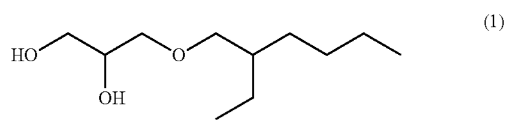

(1)

Even more particularly, ethylhexylglycerin is a chemical compound that is a direct derivative of glycerine. It is derived from synthetic raw materials. It is generally deemed to be considered very safe and a non-irritant to skin. Further, ethylhexylglycerin (or ethyl hexyl glycerin) is known for its deodorizing properties, acts as a preservative (as described hereinabove), and as an active skin conditioning agent. It has extensive use as an alternative to parabens in cosmetic preparations since parabens have been time and again, identified as a source of several critical diseases in humans. Ethylhexylglycerin also is considered an active surfactant. When it comes to using the chemical as a preservative, ethylhexylglycerin works very well, even in small amounts and makes it an economical choice for mass producing cosmetic plants. In many types of research, it has been proven for use as an enhancer for cosmetic preparations, thereby replacing parabens. The chemical, ethylhexylglycerin also arrests the growth of bacteria that causes body odor without disturbing the beneficial bacteria present on the human skin in any skin or scent-based formulations. Ethylhexylglycerin is known for its ability to boost the efficiency and efficacy of all known traditional preservatives. Further, ethylhexylglycerin also acts as a stabilizer in cosmetic or fragrance preparations that keeps microbial life in check. The chemical is highly pure, colorless and carries a mild odor that is negligible, except for perhaps, a well-trained nose (in French: nez) or fine perfumer, essentially due to their fine sense of smell and skill in producing olfactory compositions. This is of particular importance to a fragrance-based hair product where any additional ingredients are intended to maintain integrity of the original fragrance notes and permit uniformity and slow diffusion thereof. Ethylhexylglycerin partakes in maintaining the original fragrance integrity of the hair mist formulation.

In a moisturizing formulation embodiment, ethylhexylglycerin is an impressive skin and/or hair moisturizing agent. It is known to improve the overall texture of cosmetic formulations for the skin and other formulations for hair. In example embodiments comprising fragrance-based formulations, ethylhexylglycerin helps in boosting the effects of fragrance ingredients and properly stabilizes and/or fixes the fragrance ingredients to the formulations. In certain implementations, ethylhexylglycerin also helps to reduce the surface tension between the various liquids and oils in beauty products. The chemical, ethylhexylglycerin, is a commonly used ingredient in skincare products, and also used in haircare products. Ethylhexylglycerin is also known to improve the skin feel of cosmetic and/or fragrance-based formulations for skin, and also applied to other formulations for hair. It essentially serves as a multi-functional ingredient in the cosmetic industry. Ethylhexylglycerin also boosts antimicrobial efficacy and enables lower concentrations of typically used preservatives including parabens or triclosan, and thus, is considered a multifunctional preservative component with emollient and humectants functionality.

In certain aspects or embodiments, a known chemical formula for ethylhexylglycerin is $C_{11}H_{24}O_3$. The IUPAC name is 3-[(2-Ethylhexyl)oxy]-1,2-propanediol. Another name for same chemical is Octoxyglycerin.

In certain embodiments of the disclosed fragrance carrier formulation for hair mist product, other fragrance diluents such as glycols (dipropylene glycol, 1,3 propanediol, propylene glycol), esters (isopropyl myristate, isopropyl palmitate), natural oils (vegetable oil, jojoba oil), glucose ethers (propoxylated methyl glucose ether), and/or glycerin esters (caprylic/capryl glycerin) may be added to the formulation.

More particularly, ethylhexylglycerin is a chemical compound that is a direct derivative of glycerine. Ethylhexylglycerin is derived from synthetic raw materials. Ethylhexylglycerin is generally deemed to be considered very safe and a non-irritant to skin. Further, ethyl hexyl glycerin is known for its deodorizing properties, acts as a preservative, and as an active skin conditioning agent. It has extensive use as an alternative to parabens in cosmetic preparations since parabens have been time and again, identified as a source of several critical diseases in humans. Ethylhexylglycerin also is considered an active surfactant. When it comes to using the chemical as a preservative in such hair product formulations, it works very well, even in small amounts and renders it an economical choice for mass producing cosmetic plants. In many types of research, ethylhexylglycerin has proven for use as an enhancer for cosmetic or hair type preparations, thereby replacing parabens. The chemical also arrests the growth of bacteria that causes body odor without disturbing the beneficial bacteria present on the human skin in any skin or scent-based formulations. Ethylhexylglycerin is known for its ability to boost the efficiency of all known traditional preservatives. Further, ethylhexylglycerin also acts as a stabilizer in cosmetic or other fragrance preparations, including hair fragrance-based formulations, that keeps microbial life in check. The chemical is highly pure, colorless and carries a mild odor that is negligible, except for perhaps, a well-trained nose or fine perfumer.

In certain aspect or embodiments, the propanediol ingredient of the disclosed hair mist fragrance formulation and product, can be any suitable propanediol for non-aerosol hair sprays, including hair mist sprays. A preferred propanediol is 1,3 propanediol, also known as trimethylene glycol, with IUPAC name propane-1,3-diol. Other propanediols, glycols, or similar compounds known in the art can be used, such as propylenene glycol, butylene glycol, pentalene, hexylene glycol, or other straight chain glycols with carbon chain lengths of up to about 8. The benefit of a Zemea version of this ingredient or material is that it is bio-derived from bioconversion of natural grains, so it's considered a natural material.

In certain aspects or embodiments, the present hair-mist fragrance carrier formulation is preservative-free, and specifically, preserved naturally because of naturally derived zemea (1,3 propanediol) (or similar ingredient) which has natural bacteriostatic properties. In particular, zemea delivers a multifunctional, preservative-boosting humectant and such ingredient delivers high performance in a variety of applications—including cosmetics, hair products, and fragrances. Zemea is considered sustainably sourced and generates up to 40% less greenhouse gas emissions over its life. Moreover, in accordance with certain embodiments, a natural preservative enhancer (for example, zemea) and/or even some pigments can be added to the formula to naturally preserve the product from bacteria contamination and to improve the aesthetics thereof.

Propanediol is derived from corn, while propylene glycol is found from petrochemicals. Even though propylene glycol is considered to be safe in most cosmetics products, propanediol is widely used as an alternative for propylene glycol, especially for those consumers that desire glycol-free products.

The alcohol ingredient of the hair mist product can be any suitable alcohol for hair mist sprays. A preferred alcohol is ethanol, for example SDA 40B ethanol 190 proof, but other suitable alcohols known in the art can be used.

A wide range of additives suitable for a hair mist product may also be used, including, for example, proteins, amino acids, biological additives, Aloe Vera, vitamin E (tocopherols) and other vitamins, and panthenol.

The hair mist product in disclosed embodiments, contains no quaternium or cationic compounds, and is free of silicone, which can weigh down the hair. The disclosed hair mist product is paraben-free, sulfate-free, phthalate-free, VOC compliant (as described hereinabove), long lasting, and enhances hair shine, non-greasy, silky feel. Quaternium compounds are under safety scrutiny in the industry. Silicones and silicone polymers have a negative consumer perception not being natural. Delivering a light and non-sticky feel and clear formulation with low alcohol is a challenge and this disclosed formulation delivers both consumer desired benefits. The strict VOC (volatile organic compound) restrictions for hair care products in the United States (and even other countries outside the U.S.), are met by the disclosed formulation, in particular with respect to the level of ethanol, as it meets or falls below the relevant U.S. restrictions.

The disclosed subject matter is a California Air Resources Board (CARE) and VOC-compliant hair mist product with less than 50 VOC. The disclosed hair mist procut is silicone-free and will not build up on the hair unlike traditional hair fragrance products, which typically contain silicones or silicone polymers. The hair mist product contains fragrance substantive materials to enhance fragrance freshness on the hair for several hours, up to 8-12 hours. The hair mist product is not greasy and rinses easily from the hair when washed. Although fragrance oils may be used, as discussed above, the combination of the other ingredients in the non-aerosol hair mist product leaves a non-oily, silky, and luxurious feel when applied to one's hair.

In certain aspects or embodiments, the disclosed hair mist product, is a standard blend and fill for a hydroalcoholic fragrance mist or Eau De Toilette (EDT)-based solution. In other embodiments, an Eau De Parfum (EDP)-based solution is contemplated. In accordance with an embodiment, the hair mist product comprises less than 45 percent VOC and contains a level of water of that complies with VOC restrictions of less than 50-55 percent for haircare products under the category of hair finishing spray. The combination of propanediol and ethylhexylglycerin enhances the fragrance substantivity, without rendering the hair feel as heavy or oily.

For purpose of explanation and illustration, and not limitation, exemplary embodiments and trials of the hair mist product in accordance with the disclosed subject matter are described herein below.

Example 1

Table 1 hereinbelow lists the ingredients and composition of a hair mist product in accordance with an example implementation of the present disclosure.

TABLE 1

| INGREDIENT | WEIGHT % |
|---|---|
| Phase A | |
| Fragrance | 10.0 |
| Solubilizer | 9.5 |
| Ethylhexylglycerin | 4.4 |
| Propanediol | 2.0 |
| Alcohol | 47.0 |
| Phase B | |
| Water | 27.0 |
| Amino Acid Complex Additive | 0.1 |

Trial 1:

An informal panel was conducted to assess the user response for the hair mist product. The product was first sprayed on the hair of three (3) participants. Throughout the day, thereafter, the participants were asked to rate the strength and duration of the fragrance. The results showed that the product lasted for more than 8 hours. Participants were also requested to wash and rinse the product from their hair. These participants were next asked whether the product was heavy or weighed down the hair, and the panelists (i.e. participants) each responded that the product did not result in heavy or weighed down the hair.

Example 2

Table 2 lists the ingredients and composition of a hair mist product in accordance with an example implementation of the present disclosure.

TABLE 2

| HAIR MIST TRIAL<br>% Range/TRADENAME | | | | |
|---|---|---|---|---|
| No. | Trade Name | INCI name Mix | Range | Function |
| 1 | ETHANOL SDA 40B 190 PROOF (Greenfield-Pharmco)* | ALCOHOL DENAT.<br>WATER (AQUA) | 38-50% | SOLVENT<br>SOLVENT |
| 2 | FRAGRANCE | FRAGRANCE (PARFUM) | 0.1-15.0% | FRAGRANCE |
| 3 | SOLUBILIZER (Symrise#) | PEG-40 HYDROGENATED CASTOR OIL<br>TRIDECETH-9<br>WATER (AQUA) | 5-10% | SOLUBILIZER<br>SOLUBILIZER<br>SOLVENT |
| 4 | SENSIVA SC50 | ETHYLHEXYL GLYCERIN | 3.0-4.9% | MULTIFUNCTIONAL |
| 5 | ZEMEA | 1,3 PROPANEDIOL | 0.5-5.0% | MULTIFUNCTIONAL |
| 7 | WATER | WATER (AQUA) | 38-45% | SOLVENT |
| | Total | | | |

*CONTAINS SD ALCOHOL 40B 190 PROOF

Additives at levels 0.01-15%

Formula may contain Proteins, or amino acids

Biological additives without odor *Aloe Vera*,

Vitamins Panthenol, vitamin E (tocopherols)

It is noted that the blend of solubilizer shown in TABLE 2, comprises a mixture and is a preferred exemplary bend that can be substituted for another blended material, with similar chemical blends, in certain aspects or embodiments. In certain aspects or embodiments, the 2,3 Propanediol can be replaced by propylenene glycol, butylene glycol, pentalene or hexelene glycol or straight chain glycols with a maximum Carbon length of 8. It is further noted that one or more formulations of the hair mist product may comprise one or more of: proteins, amino acids, and/or biological additives without odor, Aloe Vera, vitamins, Panthenol, and/or Vitamin E (tocopherols).

The Abstract is provided to comply with 37 C.F.R. § 1.72(b), which requires an abstract that will allow one upon review to quickly ascertain the nature of the technical disclosure. The Abstract generally permits one to determine quickly from a cursory inspection of thereof, the nature and gist of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

The foregoing description of exemplary embodiments, including examples, is presented only to describe, explain, and illustrate the broad concepts of the disclosed subject matter, and is not intended and should not be construed to limit the scope of the of the present disclosure. Various modifications and improvements may be made by those skilled in the art without departing from the scope. Thus, the disclosed subject matter includes all modifications and improvements that are within the scope of the following claims and their equivalents. All of the disclosed and claimed embodiments can be made and implemented without undue experimentation in light of the present disclosure. Thus, the disclosed subject matter includes all modifications and improvements that are within the scope of the following claims and their equivalents.

What is claimed is:

1. A non-aerosol, non-oily, and uniformly diffusive hair mist formulation comprising:

fragrance element, in an amount of about 0.1 to 15.0 percent by weight;

a fragrance solubilizer, in an amount of 5.0 to 10.0 percent by weight;

ethylhexylglycerin, in an amount of 3.0 to 4.9 percent by weight;

propanediol, in an amount of 0.5 to 5.0 percent by weight;

an alcohol solvent, in an amount of 38.0 to 50.0 percent by weight; and water, in an amount of about 20 to 35.0 percent by weight;

wherein, the hair mist formulation is silicone-free, associated with longevity and uniform application of fragrance, including an extended release of volatile fragrance top notes with lasting integrity of original fragrance notes with improved fragrance lift, and imparting hair with greater shine and silky feel.

2. The hair mist formulation of claim 1, further comprising:

an additive in an amount of 0.01 to 15.0 percent by weight.

3. The hair mist formulation of claim 2, wherein the additive is one or more of a protein, amino acid, biological additive, Aloe Vera, vitamin, and panthenol.

4. The hair mist formulation of claim 2, wherein:

the fragrance element, is in an amount of 10.0 percent by weight;

the solubilizer, is in an amount of 9.5 percent by weight;

the ethylhexylglycerin, is in an amount of 4.4 percent by weight;

the propanediol, is in an amount of 2.0 percent by weight;

the alcohol solvent, is in an amount of 47.0 percent by weight;

the water, is in an amount of 27.0 percent by weight; and the additive, is in an amount of 0.1 percent by weight.

5. The hair mist formulation of claim 4, wherein the additive comprises one or more amino acid(s).

6. The hair mist formulation of claim 1, wherein the fragrance comprises eau de toilette or eau de parfum.

7. The hair mist formulation of claim 1, wherein the hair mist formulation is capable of being dispensed uniformly using a mechanical pump mechanism.

8. The hair mist formulation of claim 1, further comprising longevity of shine upon application thereof.

9. The hair mist formulation of claim 2, wherein the additive is one or more of a combination of a protein, amino acid, biological additive, Aloe Vera, vitamin, and/or panthenol.

10. The hair mist formulation of claim 2, wherein the additive comprises one or more amino acid(s).

11. The hair mist formulation of claim 1, further comprising the hair mist formulation is VOC compliant.

12. A non-aerosol, non-oily, and uniformly diffusive hair mist formulation comprising:

fragrance element, in an amount of about 0.1 to 15.0 percent by weight;

a fragrance solubilizer, in an amount of 5.0 to 10.0 percent by weight;

ethylhexylglycerin, in an amount of 3.0 to 4.9 percent by weight;

propanediol, in an amount of 0.5 to 5.0 percent by weight;

an alcohol solvent, in an amount of 38.0 to 50.0 percent by weight; and water, in an amount about 20 to 35.0 percent by weight;

wherein, the hair mist formulation is silicone-free, associated with longevity and uniform application of fragrance including an extended release of volatile fragrance top notes with lasting integrity of an fragrance note with improved fragrance lift, and imparting hair with greater shine and silky feel.

13. The hair mist formulation of claim 1, wherein the fragrance comprises perfume compounds that include fragrance notes, present from about 1 to lower than 20% by weight.

14. The hair mist formulation of claim 13, wherein the fragrance notes are present from about 5% to 13% by weight.

15. The hair mist formulation of claim 12, wherein the fragrance comprises perfume compounds that include fragrance notes, present from about 1 to lower than 20% by weight.

16. The hair mist formulation of claim 15, wherein the fragrance notes are present from about 5% to 13% by weight.

17. The hair mist formulation of claim 1, that comprises an additive that extends the release of volatile top notes and slows diffusion thereof.

18. The hair mist formulation of claim 12, that comprises an additive that extends the release of volatile top notes and slows diffusion thereof.

19. A method of treating hair that comprises application of the hair mist formulation of claim 1.

20. A method of treating hair that comprises application of the hair mist formulation of claim 12.

* * * * *